United States Patent [19]
Miola et al.

[11] Patent Number: 6,010,669
[45] Date of Patent: Jan. 4, 2000

[54] METHOD FOR RESTORING THE FUNCTIONALITY OF EQUIPMENT SUBJECTED TO HEAVY CORROSION IN A PLANT FOR THE PRODUCTION OF UREA

[75] Inventors: Cesare Miola, Pavia; Franco Granelli, Milan, both of Italy

[73] Assignee: Snamprogetti S.p.A., San Donato Milanese, Italy

[21] Appl. No.: 08/793,928

[22] PCT Filed: Sep. 8, 1995

[86] PCT No.: PCT/EP95/03539

§ 371 Date: Mar. 21, 1997

§ 102(e) Date: Mar. 21, 1997

[87] PCT Pub. No.: WO96/09136

PCT Pub. Date: Mar. 28, 1996

[30] Foreign Application Priority Data

Sep. 22, 1994 [IT] Italy .................................. MI94A1924

[51] Int. Cl.[7] ...................................................... B01J 19/02
[52] U.S. Cl. ........................ 422/241; 228/184; 228/189; 228/594; 228/599; 228/603; 228/636
[58] Field of Search ............................ 422/241; 228/184, 228/189, 594, 595, 599, 603, 636

[56] References Cited

U.S. PATENT DOCUMENTS 3,986,243 10/1976 Schussler et al. .

4,600,139 7/1986 Murase .

FOREIGN PATENT DOCUMENTS 2052929 5/1972 Germany .
2239975 2/1973 Germany .
3720603 1/1989 Germany .

OTHER PUBLICATIONS

Patent Abstract of Japan, vol. 12, No. 149 (M–694) May 10, 1988 of JP–62–270894.

Primary Examiner—Timothy McMahon
Attorney, Agent, or Firm—Oblon, Spivak, McClelland, Maier & Neustadt, P.C.

[57] ABSTRACT

A method for repairing and restoring the functionality of equipment subjected to internal corrosion during its operation at high or medium pressure in a plant for the synthesis of urea. The method includes the cleaning of the corroded area, the formation of suitable supporting and/or holding surfaces for the placement of a new metallic lining, the formation of a new anticorrosive sealed off lining, obtained by positioning and welding flat elements and metallic plates which are suitably shaped and placed next to each other to become adapted to the internal profile of the equipment. The spaces and interstices below this new lining all communicate with at least one weep-hole present in the pressure resistant body. The entire repair is carried out through the manhole of the equipment and enables the restoring of its functionality for times similar to the normal duration of corresponding newly constructed equipment.

16 Claims, 4 Drawing Sheets

METHOD FOR RESTORING THE FUNCTIONALITY OF EQUIPMENT SUBJECTED TO HEAVY CORROSION IN A PLANT FOR THE PRODUCTION OF UREA

BACKGROUND OF THE INVENTION

1. Field of the Invention

The present invention relates to a method for restoring the functionality of equipment subjected to heavy corrosion in a plant for the production of urea.

More specifically, the present invention relates to a method for repairing and restoring the functionality of metallic parts or equipment subjected to erosion and/or corrosion by contact, under conditions of high temperature and pressure, with fluids comprising water mixed with ammonia, urea and/or ammonium carbamate, typically present in a plant for the industrial production of urea.

2. Discussion of the Background

It is well-known that urea is obtained with industrial processes which require operating conditions of high temperature and pressure at least in some parts of the plant.

In these processes, ammonia, which is generally in excess, and carbon dioxide are reacted in one or more reactors, at pressures usually of between 100 and 250 bar and temperatures of between 150 and 240° C., obtaining as end-product an aqueous solution containing urea, ammonium carbamate not transformed into urea and the excess ammmonia used in the synthesis. The above aqueous solution is purified of the ammonium carbamate contained therein by its decomposition in decomposers operating, successively, at decreasing pressures. In most of the present processes, the first of these decomposers operates at pressures which are basically the same as the synthesis pressure or slightly lower, and generally uses stripping agents to decompose the ammonium carbamate and at the same time remove the decomposition products. Stripping agents can be inert gases, or ammonia or carbon dioxide, or mixtures of inert gases with ammonia and/or carbon dioxide, and the stripping can possibly be carried out by also using the excess ammonia dissolved in the mixture coming from the reactor (self-stripping), without requiring therefore any external agent.

The decomposition products of ammonium carbamate ($NH_3$ and $CO_2$), together with the possible stripping agents, excluding the inert gases, are normally condensed in suitable condensers obtaining a liquid mixture comprising water, ammonia and ammonium carbamate, which is recycled to the synthesis reactor. In plants which are technologically more advanced, at least one condensation step is carried out at pressures more or less the same as those of the reactor or slightly lower.

As a reference, among the many in existence, patents U.S. Pat. No. 3,886,210, U.S. Pat. No. 4,314,077, U.S. Pat. No. 4,137,262 and European patent application publication No. 504,966, can be cited, which describe processes for the production of urea with the above characteristics. A wide range of processes mainly used for the production of urea is described in "Encyclopedia of Chemical Technology", 3rd Edition (1983), Vol. 23, pages 548–574, John Wiley & Sons Ed.

The most critical steps of the process are those in which the ammonium carbamate is at its highest concentration and temperature, and therefore, in the above processes, these steps coincide with the reactor and subsequent equipment for the decomposition (or stripping) and condensation of the ammonium carbamate operating in similar or almost similar conditions to those of the reactor. The problem to be solved in this equipment is that of corrosion and/or erosion caused by the ammonium carbamate, ammonia and carbon dioxide which behave as highly corrosive agents, especially in the presence of water, at the high temperatures and pressures necessary for the synthesis of urea.

This problem of corrosion has been faced with different solutions in existing industrial plants, and others have been proposed in literature. There are, in fact, numerous metals and alloys capable of resisting for sufficiently long periods to the potentially corrosive conditions which are created inside a reactor for the synthesis of urea. Among these lead, titanium, zirconium and several stainless steels such as, for example, AISI 316L steel (urea grade), steel INOX 25/22/2 Cr/Ni/Mo, austenite-ferrite special steels, etc. can be mentioned. However, for economical reasons, this type of equipment cannot be entirely made of these corrosion-resistant alloys or metals. Generally containers or columns are used in normal carbon steel, possibly multilayer, having a thickness varying from 40 to 350 mm, depending on the geometry and pressure to be sustained (pressure resistant body), of which the surface in contact with corrosive or erosive fluids is uniformly lined with an anticorrosive lining from 2 to 30 mm thick.

In particular, the reactor basically consists of a vertical "Vessel" with inlet of the reagents from below and discharge of the reaction mixture from above. The pressure-resistant body normally consists of a cylinder having a diameter of from 0.5 to 4 m, made with the multilayer or solid wall technique, having the two ends closed by caps adequately welded thereto. Inside the reactor, all parts subjected to corrosion are lined with an anticorrosive lining which can be, for example, of titanium, lead, zirconium, or preferably, stainless steels (urea grade) of the type mentioned above.

The subsequent carbamate decomposer, especially if it operates at the same pressure as the reactor, consists of a shell-and-tube exchanger. Also in this case the "pressure-resistant body" is made of normal carbon steel, whereas titanium or urea grade stainless steels are preferably used for the lining.

The gases leaving the decomposer are usually recondensed in a carbamate condenser, which is still in contact with a mixture similar to that of the decomposer (except for urea) and is therefore very corrosive. Also in this case the internal lining is preferably made up of the above special urea grade stainless steels.

In the above equipments or plant units, the anticorrosive lining is made by assembling numerous elements having a suitable resistance to corrosion, forming, at the end, a structure which is sealed off at the high operating pressure. The different connections and weldings carried out for this purpose frequently require special techniques depending on the geometry and type of parts to be connected.

Whereas stainless steel is weldable to the "pressure-resistant body" below made of carbon steel, but has a higher coefficient of thermal expansion which, during operation, favours crack formation along the welding line, titanium cannot be welded onto steel and in any case has similar problems of cracks in the welding as its expansion coefficient is considerably lower than carbon steel.

For this reason techniques are used which often require complex equipment and operating procedures. In certain cases the lining is effected by welding deposit instead of sheets welded to each other and onto the pressure body. In other cases, especially with materials which cannot be welded to each other, it is necessary to "explode" the lining onto the pressure body to be sure of obtaining a satisfactory hold.

In all the above equipment there are however a certain number of "weep-holes" to detect possible losses of anti-corrosive lining.

A weep-hole normally consists of a small pipe of 8–15 mm in diameter made of corrosion-resistant material and is inserted into the pressure body until it reaches the point of contact between the latter and the metal or alloy corrosion-resistant lining. If there is a leakage in the lining, owing to the high pressure, the internal fluid, which is corrosive, immediately spreads into the interstitial zone between lining and pressure body and, if not detected, it would cause the rapid corrosion of the carbon steel of which this latter is made. The presence of weep-holes enables these leakage to be detected. For this purpose all the interstitial zones below the anti-corrosive lining must communicate with at least one weep-hole. The number of weep-holes is usually from 2 to 4 for each ferrule and therefore, for example, in a reactor there are normally from 30 to 60 weep-holes.

The above equipment also has at least one circular opening, generally in the upper part, called "man-hole", which permits access to operators and equipment for controls and small internal repairs. These opening usually have diameters of between 45 and 60 cm and at the most allow the passage of objects having these sizes.

In spite of the numerous precautions and constructive contrivances mentioned above, it still frequently happens that large areas of the internal lining of equipment operating at high or medium pressure in contact with aggressive process fluids, such as those, for example, used in a plant for the production of urea, undergo heavy and extended corrosion which rapidly causes the risk of perforating the lining with the consequent danger of catastrophic breakages, or at the least makes it necessary to stop the plant for repairs which at times take a considerable amount of time.

Overcoming these phenomena of corrosion involves problems which are not easy to solve. Very often it is necessary to substitute the damaged equipment (reactor, exchanger or condenser) with a new one, suffering extremely high costs both for stopping the plant and for the construction and installation of the new equipment. Attempts to repair the damaged part have always been considered impossible in practice when the damage is considerable, both because of the conviction of not being able to offer a sufficient guarantee of safety for the operation and also for the practical difficulty of effecting it. Indeed, every intervention on equipment or plant units, to avoid its partial dismantling, must be carried out through the man-hole mentioned above. It is not therefore possible to insert into the equipment the metal laminates or other objects whose dimensions do not allow them to pass through the man-hole.

Considering the fact that the corroded areas are frequently extended onto surfaces of 20–30 m$^2$ or more, it is easy to understand that it is absolutely impossible to re-line the corroded area with new uniform and homogeneous lining.

Another widely diffused prejudice also concerned the problem of fixing the repair onto the previous lining. It was thought, indeed, that owing to the considerable deterioration of the metal in the corroded area, a repair involving welding and supporting zones directly in the area of interest, as well as at the edges where the previous lining still had trustworthy characteristics, was not reliable.

For this reason it was the general opinion that it was not possible to restore the functionality of lining having extended areas of corrosion, with the sole use of the man-hole.

For the many reasons mentioned above, it was generally thought unadvisable or in any case economically inconvenient to carry out operations for the repair and functional restoration of corroded lining of equipment in the section of high or medium pressure of a plant for the production of urea.

The solution normally recommended for these problems of corrosion was consequently to substitute the damaged equipment, even though this involved high costs and the necessity of interrupting the production line for relatively long periods.

SUMMARY OF THE INVENTION

The Applicant has now found a satisfactory and advantageous solution to the above drawbacks with a new approach which allows the operative restoration of the plant equipment with great reliability and without its removal, keeping the cost of repair at much lower levels than those necessary for the complete substitution of the equipment.

The present invention therefore relates to a method for the repair and functional restoration of equipment of the high or medium pressure section of an industrial plant, said equipment having at least one man-hole and comprising, internally, anticorrosive metallic lining which has at least one extended area subjected to corrosion, said method comprising the following steps:

(a) cleaning of the area subjected to corrosion, with the removal of most of the residues produced therefrom;

(b) formation, in the cleaned area according to step (a), of suitable supporting and/or holding surfaces for the placement of new metallic lining;

(c) positioning, on these supporting and/or holding surfaces and on the edges of the surface next to the corroded area, until it has been completely covered, of flat elements suitably shaped to adapt themselves to the internal profile of the equipment, and which consist of a metal resistant to corrosion under the operating conditions of the equipment and having such dimensions as to pass through the man-hole, these shaped elements being placed next to each other;

(d) welding of the adjacent edges of said elements joined to each other as in step (c) and, possibly, welding of the same edges onto the metal below them, so that this welding has at least one interrupted stretch for each single shaped element, thus forming new metallic lining resistant to corrosion in which the existing interstices between each shaped element and the surface below communicate with each other and with at least one of the weep-holes present in the body of the equipment;

(e) covering of the surface exposed to process fluids, around said interrupted welding stretches, with suitably-sized and shaped plates, welded by the edges onto the new metallic lining, in order to obtain an internal surface of the equipment which is totally sealed off and resistant to corrosion under normal operating conditions;

this repair method being entirely accomplished using the man-hole of the equipment as the only access.

The present invention further relates to the equipment obtained with the above repairing and functional restoration method.

As specified above the method of the present invention is particularly applicable to the equipment of the high or medium pressure section of a plant for the synthesis of urea.

These can be substantially identified as synthesis reactors of urea, equipment for the decomposition of the non-transformed carbamate, and containers for the condensation of $HN_3$ and $CO_2$ with the formation of carbamate solutions.

These equipments operate at pressures of between 15 and 250 atm and temperatures of between 70 and 300° C., in the presence of mixtures containing water, ammonia, carbon dioxide and ammonium carbamate which is the condensation product of these compounds according to the reaction:

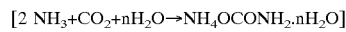
$$[2\ NH_3+CO_2+nH_2O \rightarrow NH_4OCONH_2 \cdot nH_2O]$$

The operating conditions are preferably a pressure of 100–250 atm and a temperature of 120–240° C.

Under the above conditions the surfaces of the equipment in contact with the corrosive mixtures are preferably made of stainless steel, titanium, zirconium, lead etc.. "Urea grade" stainless steel is particularly preferable, such as AISI 316L (urea grade) steel, INOX 25/22/2 Cr/Ni/Mo steel, special austenite-ferrite steels, etc. These corrosion-resistant metals or alloys do not normally form the whole body of the equipment but a lining having a thickness preferably of between 2 and 30 mm.

In normal industrial plants for the production of urea, to which the present invention particularly relates, the above equipment belonging to the high or medium pressure sections usually contain volumes of between 2,000 and 400,000 liters and have a development of the internal surfaces in contact with corrosive liquids of between 8 and 450 $m^2$, excluding the surface of possible pipes (heat exchangers, etc.). For the purposes of the present invention, equipment is considered as having extended corroded areas when its internal surface has at least one corroded zone whose area is higher than the double of the man-hole section.

The terms "corrosion", "corrosive" and "corroded" as used in the present application indifferently refer to processes comprising only corrosion of a chemical nature, or an erosion of a physical nature or a combination of both.

The method of the present invention can also be applied to equipment whose walls are not internally lined, but which is mainly made of a corrosion-resistant metal or metallic alloy. In this case, the term "internal anticorrosive lining" as used in the present application, also comprises the walls of the equipment having anticorrosive properties.

According to the method of the present invention, in step (a) it is necessary to clean the area subjected to corrosion. The corroded area normally appears as an irregular surface covered with residues caused by the corrosion (oxides, carbides, etc.) or surface layers of metal not completely corroded, but no longer integral. The irregularities (or roughness) of the surface may also be very deep and extend through a thickness varying from about 5% of the original thickness of the lining to up to 100%, in which case there is a perforation of the lining.

In step (a) of the present invention, the cleaning does not necessarily have to involve the total removal of the corrosion residues, which could prove to be too laborious in terms of time (and without any advantage), but must ensure a surface without areas with dimensional instability and without residues capable of acting as corrosion initiators during the subsequent functioning of the equipment.

In accordance with the present invention, the cleaning of the surface can be carried out using any of the methods suitable for the purpose. These comprise abrasive methods by filing, abrasive blasting, sanding, grinding, etc., or cleaning methods with solvents or suitable chemical agents capable of removing the corrosion residues thus producing a dimensionally stable layer. Cleaning methods comprising a combination of the above are not excluded. Cleaning with abrasive methods is preferred however for the purposes of the present invention.

In step (b) of the method of the present invention, appropriate supporting or holding areas are obtained on the surface suitably cleaned according to step (a), for the subsequent placing of the new lining.

According to a preferred embodiment of the present invention, in step (b) a reasonably smooth surface is obtained, in the corroded area, having a profile which is substantially in line with the profile of the previous lining in the areas adjacent to the corroded area, or where these are not present, having a profile which is preferably in line with the most prominent surface irregularities. The entire corroded area is practically covered with a first metallic layer, usually of the same material as the previous lining, of such a thickness that the new surface of this first metallic layer is brought into line with that of the lining surrounding the corroded area. The covering is carried out by fixing onto the cleaned surface, normally by welding, pre-shaped metallic elements, relatively small in dimension and with an irregular geometry, adapted to the irregularities caused by the corrosion. Alternatively, it is also possible to carry out the whole covering or part of it with welding deposits. In this way a first irregular filling is obtained which is then smoothed, with suitable techniques normally available, until a maximum depth of the residuous irregularities is reached which is preferably less than 1 mm. For the purposes of the present invention it is not necessary for this covering with a first metallic layer to be hermetically sealed with respect to the interstices below.

According to another preferred embodiment of the present invention, step (b) consists in the placing of small straps having a suitable width and thickness along the supporting lines of the metallic shaped elements subsequently positioned according to step (c). These small straps, suitably curved according to the curvature of the surface, are made of a metallic material which can be welded to the metal of said shaped elements and are preferably of the same metal. They preferably have a thickness approximately equal to that of the original undamaged lining. The width of the straps is not critical, although it enables the welding of the corrosion-resistant lining in the subsequent step (d) to be carried out more easily and with a good seal. The width of these small straps is preferably between 20 and 200 mm.

According to the present invention, the plates are placed on the underlying supporting plane without necessarily effecting any welding. Small weldings, when allowed by the project and pressure body construction codes, can be carried out to fix the strap until the placing of the subsequent layer. The plate is preferably inserted into a suitable groove formed in the corroded lining, possibly reaching the underlying metal of the pressure-resistant body. The final seal of the covering is subsequently ensured by the operations carried out in steps (d) and (e) where the weldings exposed to the corrosive fluid are in a sealed off form. The surface between the different straps can be filled as described in the previous form of embodiment of step (b), or left as such, especially if the difference of level between the surface of the plate and the surrounding area is reasonably small (so as not to jeopardize the welding seal of the successive layer with excessive deformations).

Step (c) of the process of the present invention comprises the placing, on the surface prepared according to step (b), of flat metallic elements, suitably shaped, and resistant to corrosion under the operating conditions of the equipment. In most cases and particularly in plants for the production of urea, the chemical equipment has cylindrical or at least curved sections. The above flat elements must therefore be suitably curved or shaped to adapt themselves to the surface to be lined. As they are easily deformed, the curving can be obtained with normal instruments available to an expert in the field.

The shaped elements must be arranged next to each other to facilitate the subsequent welding in step (d). The shape of the metallic elements should therefore be suitably selected so that they form a regular plane with no gaps, after positioning. A rectangular shape is preferable with most of the elements having the same dimensions. These should be such as to allow insertion into the internal part of the equipment through the man-hole, and, at the same time, also allow easy coverage of the corroded area, preferably with as few elements as possible. The present invention does not exclude however different shapes, which can be better adapted, on each occasion, to the geometries of the corroded area. The thickness of the above metallic elements varies according to the metal of which the equipment is made and the operating conditions thereof. Thicknesses of between 2 and 30 mm are preferably used.

According to a preferred aspect of the present invention, the shaped elements are made of the same metal or alloy as the original lining, or a metal or alloy which can be welded to this.

According to another preferred aspect of the invention, the metallic material of the new lining may also not be weldable to the original lining. In this latter case, in step (b) supporting and/or holding straps made of a metal which can be welded to the new lining will be suitably arranged onto the corroded surface.

The metal or metallic alloy forming the shaped elements (and new lining) of the present invention, can be selected each time from known corrosion-resistant materials under the operating conditions of the equipment. This metal or metallic alloy is preferably selected from titanium, zirconium or their alloys, or, particularly, from urea grade stainless steels such as, for example, AISI 316L (urea grade) steel, INOX 25/22/2 Cr/Ni/Mo steel, austenite-ferrite special steels, etc. The selection of a material which has a higher corrosion-resistance (however measured) than the original lining is left to the expert in the field.

The arranging of the shaped metallic elements can be carried out using all the conventional methods available to the expert in the field, provided that they are compatible with the operating conditions of the equipment. Mechanical fastenings or welding points can normally be used.

Step (d) of the method of the present invention comprises the welding of the shaped metallic elements according to what is described for step (c). The welding method is not critical and any of the methods available in the known art can be used, as long as it guarantees weldings having resistance to corrosion and mechanical properties which are suited to the operating conditions of the equipment.

The welding is preferably carried out with arc electrodes, or "T.I.G." with wire rods. The adjacent edges of the metallic elements placed next to each other are welded to each other and, preferably, the same edges are welded onto the underlying supporting surface.

At least one stretch on the edge of each metallic element is systematically left unwelded. This unwelded part, which forms a connecting point between the interstitial space below each element and that of the adjacent element, preferably has a length of between 5 and 30 mm. The number of unwelded stretches varies according to the type and geometry of the equipment and the number of existing weep-holes, and, on an average, is preferably between, 1.5 and 2.5 unwelded stretches per shaped element. The distribution of these is not necessarily homogeneous. In short, for the purposes of the present invention, both the unwelded parts and the consequent communicating points must allow a fluid released in any interstitial space below the new lining, to reach at least one of the weep-holes present in the pressure-resistant body of the equipment. It is not necessary however for all the interstitial spaces (or areas) to communicate with each other, communication with the weep-hole is sufficient.

A particular aspect of the present invention relates to the case where, in step (c) shaped elements of a metal or metallic alloy are used which cannot be welded to the material of which the new lining is made. In fact, in this case, unless the whole equipment is covered with new lining, these shaped elements must be welded as to be sealed off to the edges of the corroded area, in order to create a stable, impermeable and corrosion-resistant connection. Perhaps, in this case the new lining cannot be directly welded onto the previous one, nor is it sufficient to position a strap onto the edge, which is weldable to the new lining, as this does not guarantee sufficient seal against fluids at high or medium pressure.

With respect to this particular aspect of the present invention, the above drawback can be easily overcome with the help of a suitable bimetallic strap. This preferably consists of two straps, one which is weldable to the metal of the new lining and the other which can be welded to the metal of the original lining, which are structurally joined to each other by one face, with physical methods, thus obtaining a sealed off connection for the whole length of the strap. The two straps can also be connected on only part of the joining face to obtain an irregular structure as schematically shown in FIG. 5. The hermetically sealed connection in the bimetallic strap is preferably obtained by exploding the two straps to be joined against each other, according to the techniques known to experts in the field.

In step (e) of the method of the present invention, the stretches of interrupted welding between the shaped metallic elements are covered, by placing metallic straps, suitably shaped on top of these, and subsequently seal-welding the edges onto the underlying metal. This operation must be carried out in such a way as to guarantee that the total surface exposed to process fluids in the equipment is sealed off, but maintaining the communication between the interstitial spaces underneath the new lining. The welding onto the edges of each metallic strap is carried out using one of the methods normally available and, preferably, with one of the methods previously mentioned in the description of step (d).

Plates suitable for the purposes of the present invention have appropriate dimensions for covering the entire length of the interruption stretches and are preferably square or rectangular in shape. The dimensions are preferably between 20 and 200 mm. The thickness of the straps is preferably between 4 and 25 mm. These plates are preferably made of the same metal or alloy as the shaped elements which form the new lining, but can also be of a different material, provided that it can be welded to these.

In accordance with the method of the present invention, and with reference to what is specified above, the covering of the stretches of welding according to step (e) permits maintainance of the communication of each interstitial area under the lining with at least one weep-hole and, at the same time, guarantees that the surface in contact with the process fluids is sealed off. In this way the functionality of the equipment is totally restored, with the guarantee that the control and safety standards are maintained.

The weep-holes originally present in the equipment are preferably extended to beyond the border of the original lining, to reach the border of the new lining, to provide or facilitate communication with the interstitial areas. It may occasionally be necessary to produce a new weep-hole where the corroded area does not have a sufficient number thereof.

According to a particular form of embodiment of the present invention, steps (c) and (d), or also steps (c), (d) and (e) can be carried out contemporaneously, in the sense that each of the above steps can be carried out independently in different points of the area subjected to corrosion. For example, the placing of the shaped elements of step (c) can be carried out in a certain area of the operating zone, and the welding of these elements (step (d)) initiated while the positioning of other shaped elements can be continued in a different area, preferably adjacent. Naturally, in each single point of the corroded area, the operation according to the present invention must be carried out following the different steps in the order previously specified.

The method of the present invention is suitable for the functional restoration of areas subjected to corrosion, which can vary a great deal in extent and depth. When the corroded areas are very widespread or even when the corrosion involves the whole internal surface of the equipment, the present method gives particularly advantageous results.

In particular, the method of the present invention permits the original functionality of equipment to be completely restored, fully according to the safety regulations. It has also been surprisingly discovered that, although the new lining has a considerable number of welding lines, this does not prejudice its duration, thus ensuring good functioning of the equipment for the normal times estimated for corresponding new equipment.

The repair operation of the present method also permits excellent safety control of the whole equipment, particularly with respect to identifying possible leakage of the new lining, without having to produce further weep-holes in the pressure body or, possibly, producing a very limited number thereof (which does not exceed 20% of the original density of the weep-holes in the local area subjected to corrosion). There is therefore the further advantage of having a less complex repair operation.

Although the present method is particularly suitable for the functional repairing of equipment operating in a plant for the production of urea, the scope of the present invention does not exclude its application, or a method equivalent thereto, to equipment operating in different plants at medium or high pressures and/or temperatures, but having similar problems of widespread corrosion and difficulties of repair.

BRIEF DESCRIPTION OF THE DRAWINGS

The applicative characteristics of the method of the present invention can be better understood if reference is made to the drawings, schemes and photographs shown in the enclosed figures, wherein.

DISCUSSION OF THE PREFERRED EMBODIMENTS

Figure 1:
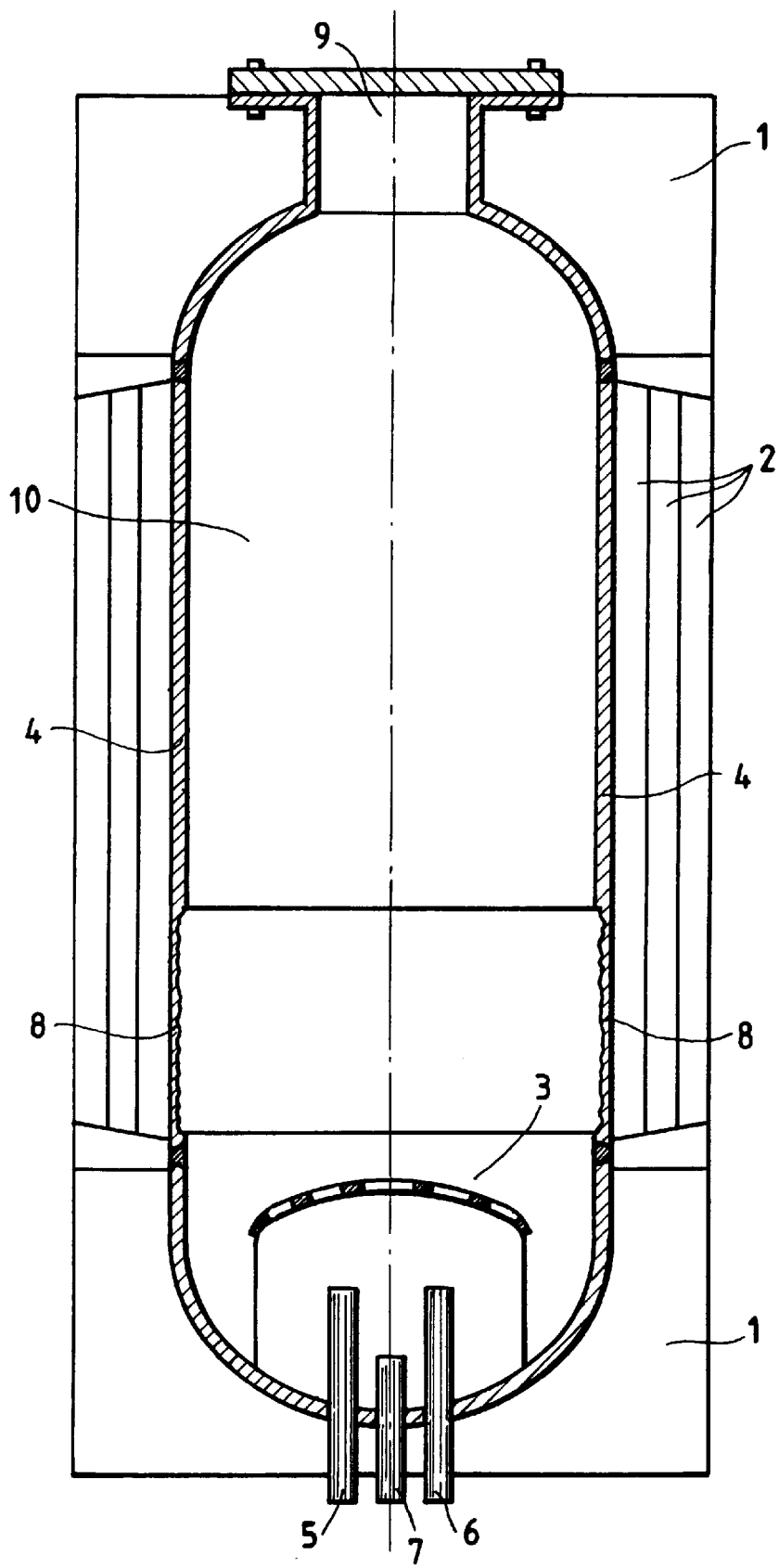
FIG. 1 schematically represents a view of the longitudinal section of a reactor for the synthesis of urea.
Figure 2:
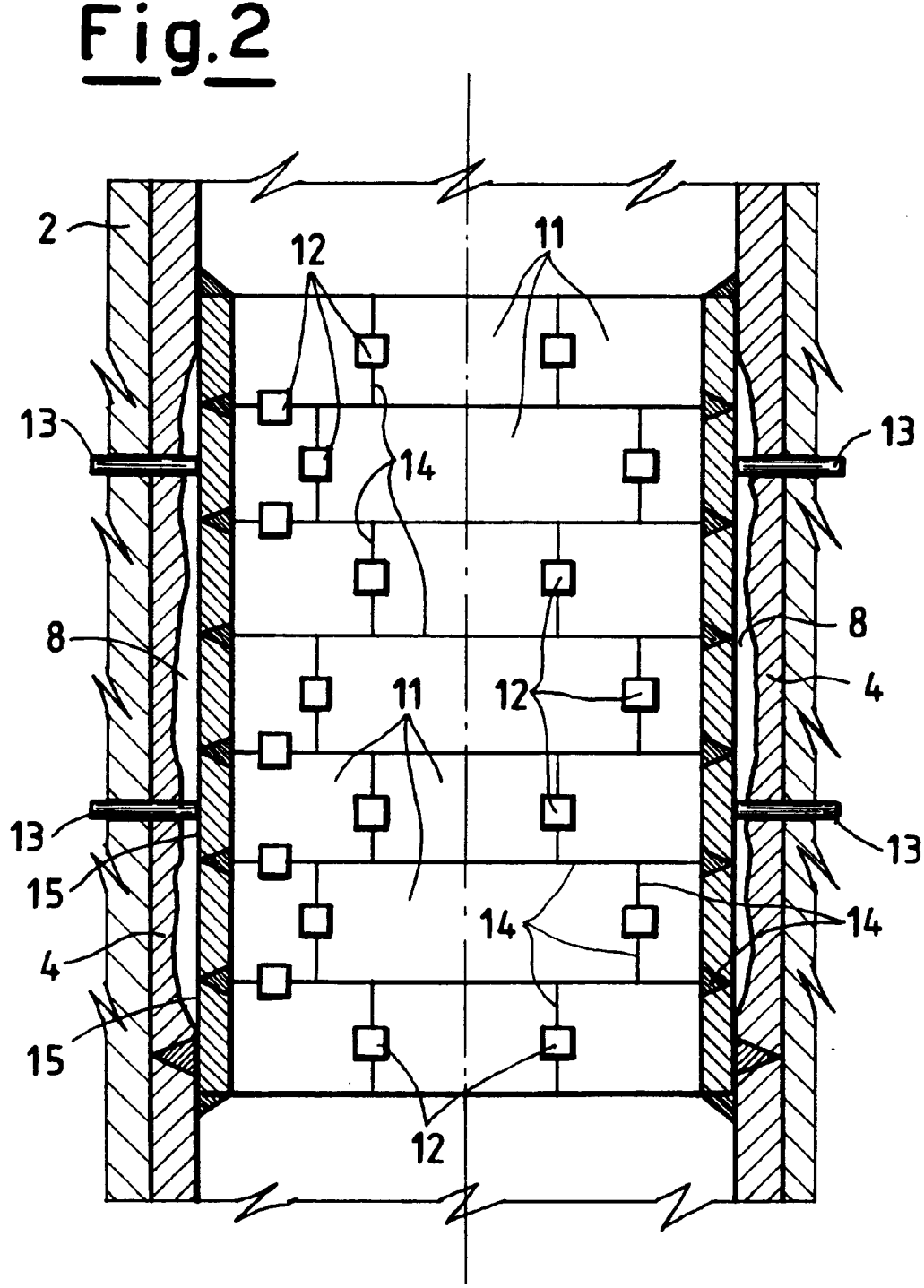
FIG. 2 schematically represents an enlarged detail of the section of FIG. 1, relating to the area particularly subjected to corrosion, after the functional restoration of the present invention.
Figure 3:
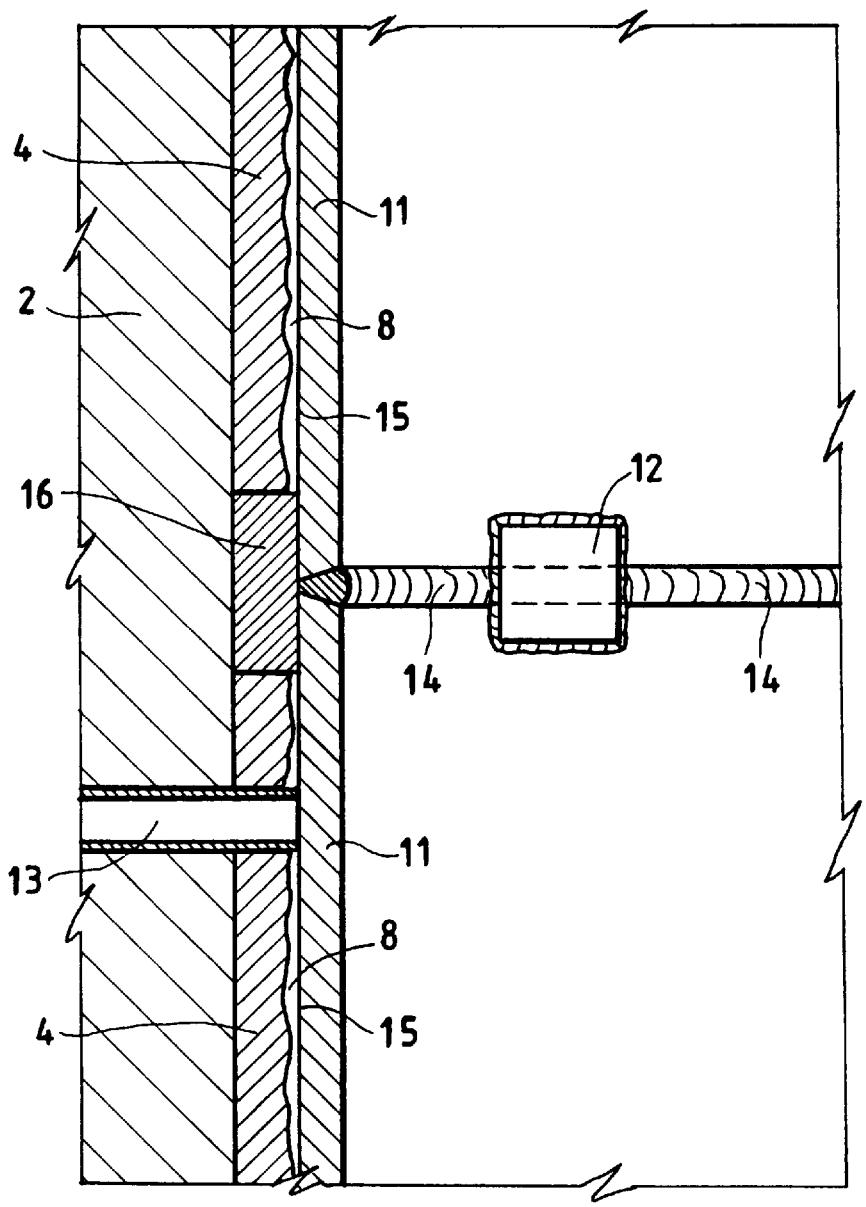
FIG. 3 schematically represents a detail of the longitudinal section of a reactor subjected to corrosion, after the functional restoration of the corroded area using the positioning of straps in step (b) of the method of the present invention.
Figure 5:
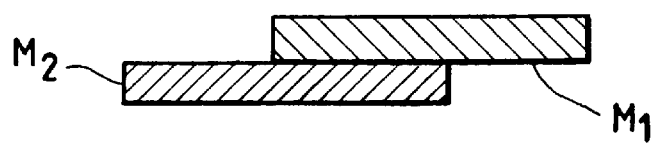
FIG. 5 schematically represents the section of a bimetallic strap wherein two straps of two metals $M_1$ and $M_2$, not weldable to each other, are partially joined by a face to form a staggered structure.

In the figures, corresponding parts have identical reference numbers for the sake of simplicity. In FIGS. 1, 2 and 3 the different elements are not drawn to scale to provide a better illustration of the distinctive characteristics of the present invention. The different figures enclosed illustrate the present invention but do not limit it in any way.

In FIG. 1, the reactor basically comprises the pressure-resistant body in which there are the forged caps 1 and the multilayer cylindrical body 2, which is internally lined with a metallic lining 4 normally resistant to corrosion. The reactor terminates above with a man-hole 9, with relative blind flange. In the lower side there are the inlet lines for ammonia 5, carbon dioxide 6 and aqueous carbamate solution 7 coming from the recycling of the reagents not transformed into urea, as well as the ring 3 which acts as a streams distributor. On the middle lower side of the reactor, circularly arranged around the internal jacket, is the area subjected to corrosion 8, whose functionality has been restored according to the method of the present invention. Any possible supporting and control equipment is not shown in FIG. 1, and neither are the weep-holes or safety valves.

In the section of the reactor represented by FIG. 2, the pressure-resistan body 2 can be seen again and also the original lining of the reactor 4 which has undergone corrosion up to an approximate depth schematically represented by section 8. Placed on top of corrosion area 8 is the new lining consisting of the shaped elements 11 welded to each other on lines 14. In numerous points of the welding lines 14, there are the metallic straps 12, welded by the edges to the elements 11. Below the straps 12, and not shown in FIG. 2, are the stretches of interrupted weldings, to allow communication between the interstitial areas 15 situated between the elements 11 and supporting areas beneath these. On the sides of the reactor four weepholes 13 are schematically shown.

FIG. 3 shows again most of the components previously mentioned with reference to FIG. 2, i.e.: the pressure-resistant body 2, the original lining of the reactor 4, the area subjected to corrosion 8, the shaped elements 11 welded to each other on the lines 14, the metallic strap 12, the interstitial areas 15 and the weep-hole 13. FIG. 3 also schematically represents in the section the strap 16 which forms the support of the welding line 14 between two shaped elements 11, the latter not being weldable to the metal of the previous lining 4.

After this both general and detailed description of the present invention, a practical example follows for its embodiment, without limiting however the scope of the invention in any way.

EXAMPLE

The repairing and functional restoration was carried out of the internal anticorrosive lining of a reactor of a plant for the production of 600 tons/d of urea.

This reactor operated at 230 bar and 190° C., with a reaction mixture comprising, under steady conditions, $NH_3$, $CO_2$ and urea, water and air as passivating agent. The reactor, according to the scheme of FIG. 1, basically comprised a vertical Vessel consisting of a cylindrical multilayer pressure-resistant body 2 (thickness 3×47 cm), having an internal diameter of 1.5 m and a length of 17.2 m, and two hemispherical forged caps 1 at the upper and lower ends. On the upper end was the man-hole 9, circular and with a diameter of about 550 mm. The internal anticorrosive lining 4 was made of AISI 316L steel, urea grade and had a thickness of about 17 mm. The internal volume of the reactor was about 32,000 liters, with an internal surface extension of the pressure-resistant body of about 85 m². In the pressure vessel there were a total of 26 weep-holes at suitable distances from each other. A wide cylindrical segment 8 in the lower middle part of the reactor had undergone corrosion for a height of about 4 meters and a total surface area of about 18 m². The corrosion involved an average depth of 11 mm in the lining.

After testing the integrity of the pressure-resistant body, and ensuring that no infiltration of process fluids had attacked the carbon steel, the surface of the lining in the corroded area was brushed to remove most of the corrosion residues and possible unstable metallic layers. The more evident irregularities of the surface, and particularly the points where the cavities due to the erosion were at their deepest, were filled with 25/22/2 Cr/Ni/Mo steel strips having a thickness of from 3 to 5 mm, fastened to the previous lining by tack weld. The remaining less deeply corroded areas were filled with AISI 316L urea grade steel welding deposit. The whole corroded surface was then reasonably smoothed by filing and grinding. A satisfactory supporting surface was thus obtained by practically filling the cavity due to erosion and schematized by section 8 in FIG. 2.

The weep-holes 13 present in the corroded area were extended through the pre-existing partially corroded lining and filling metallic layer fixed as described above.

A new lining was fixed on the surface thus prepared, obtained by joining the rectangular metal sheets 11 (metal elements) made of 25/22/2 Cr/Ni/Mo stainless steel having a thickness of 5 mm, appropriately curved (shaped) to favour a homogeneous support and well distributed onto the surface of the reactor. Each metal sheet was fastened by tack weld. The dimension of each sheet was about 400×1500 mm, to be easily inserted through the man-hole. The resistance to corrosion of the metal sheets was checked on samples submitted to the anti-corrosion test according to regulation "ASTM A-262, Practice C", in which there resulted to be absence of corrosive phenomena. The sheets were arranged to completely cover the corroded area, until they were partially overlapping, on the border of this area, the previous lining undamaged by corrosion.

The metal sheets were then arc welded to each other, along the adjacent edges, using an alloy having the same composition as the sheets for the welding. Stretches of interrupted welding, from 10 to 20 mm in length, were left along the welding line, so that all the areas below the metal sheets communicated with at least one weep-hole. For this purpose no particular geometric regularity was followed, only keeping into account the fact that a series of communications branched out around each weep-hole from one metal sheet to another, thus connecting all the underlying intestices up to vicinity of the successive weep-holes.

The external part of each stretch of interrupted welding was subsequently covered with a plate, of the same nature as the material of the reactor, which was square-shaped with a side of about 40–50 mm. The thickness was again 5 mm. The edges of each strap were welded in the same way as the lining sheets.

The welding of the metal sheets to the previous lining (made of AISI 316L urea grade, weldable to 25/22/2 Cr/Ni/Mo steel) was then carried out along the entire edge of the new lining thus obtained (covering the whole corroded area), thus ensuring that the whole lining of the reactor was hermetically sealed.

At the end of the operation, each of the interstitial spaces 15 underneath the new lining communicated with one or even two weep-holes without it being necessary to make any additional weep-hole, with respect to those originally existing in the pressure-resistant body.

Figure 4A:
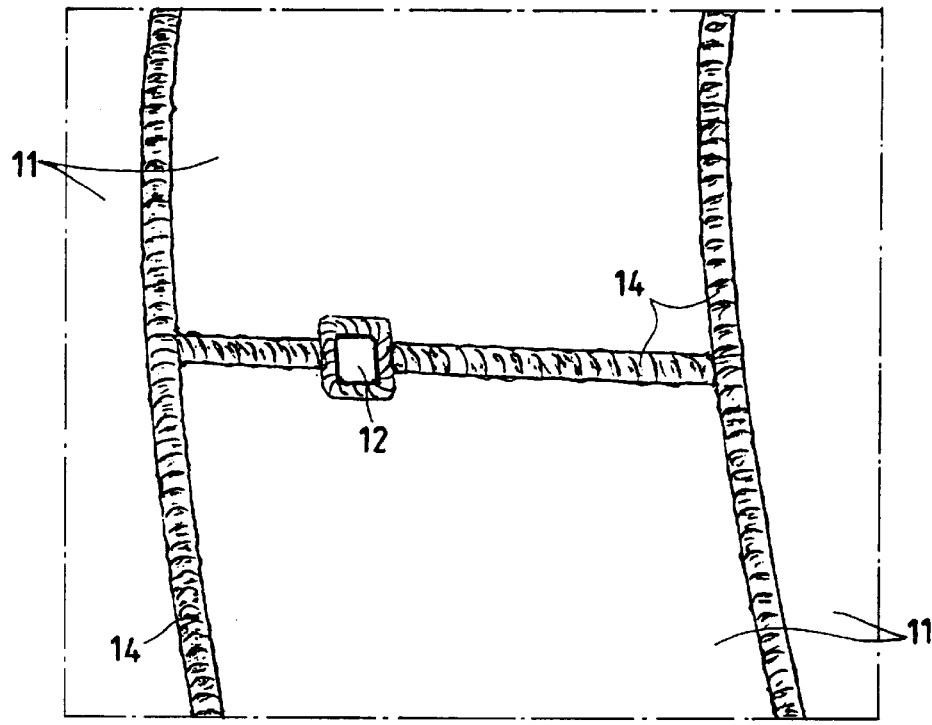
FIG. 4A reproduces a photograph of a strap welded onto the metallic lining in the communicating point between the interstitial areas under two pieces of the lining whose edges are welded together and to the underlying surface.
Figure 4B:
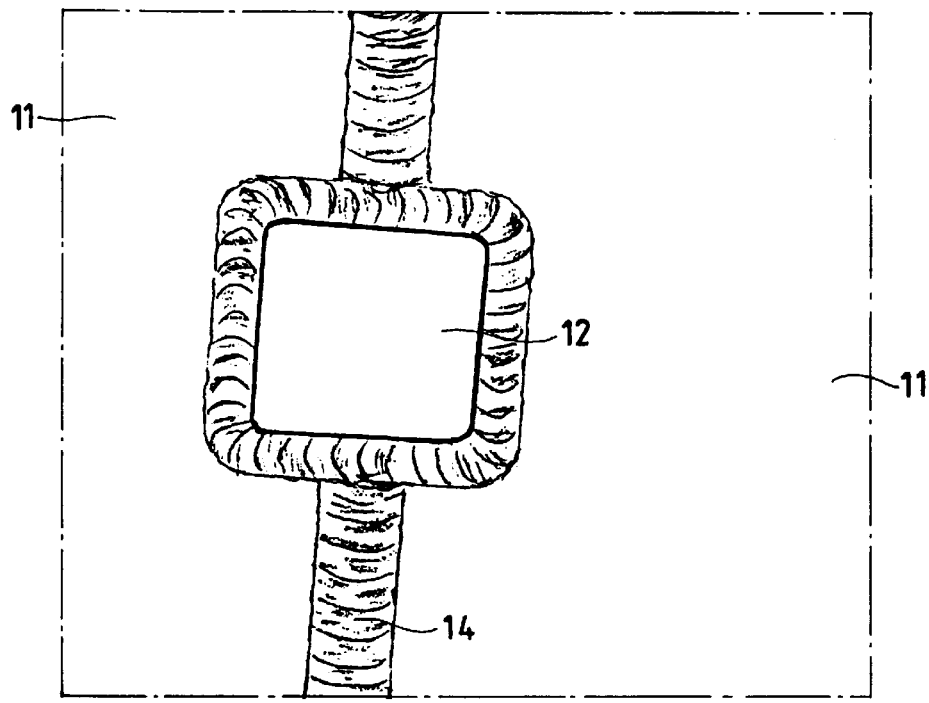
FIG. 4B reproduces an enlargement of the detail shown in FIG. 4A.

FIG. 4 shows a significant detail of the appearance of the new lining in the points where a plate has been welded covering a stretch of interrupted welding between two metal sheets.

At the end of the operation the reactor was subjected to the conventional control tests for its satisfactory working. In particular, the following tests were carried out:

Welding check with penetrating liquids according to regulation "ASME VIII, div. 1, appendix 8";

Gas seal test according to "ASME V; article 10", carried out with helium;

Pressure test, carried out by bringing the reactor inner pressure to the value specified by the project regulations (320 bar).

All the above tests gave satisfactory results.

The reactor thus repaired was subsequently operated under standard plant conditions and continued to function for at least two years, excluding the periodical interruptions for ordinary maintenance. Upon careful examination, there resulted to be no further phenomena of widespread corrosion.

What is claimed is:

1. Method for repairing and functionally restoring high or medium pressure equipment of an industrial plant, being entirely accomplished through a pre-existing man-hole of the equipment as the only access, comprising the steps of:

(a) cleaning a corroded area of an anticorrosive metallic lining of high or medium pressure equipment of an industrial plant, thereby forming a cleaned area;

(b) forming supporting surfaces on an inner surface of the cleaned area, said supporting surfaces configured for receiving and being welded to edges of liner elements;

(c) positioning liner elements on the supporting surfaces and on non-corroded portions of the inner surface of the anticorrosive lining adjacent to the cleaned area so that the cleaned area is completely covered with liner elements, wherein the liner elements and supporting surfaces are positioned so as to define a first interstitial space between the cleaned area and a liner element which does not directly communicate with a weep-hole and a second interstitial space adjacent to the first interstitial space, wherein the second interstitial space directly communicates with a weep-hole;

(d) positioning at least one strap so as to overlap adjacent edges of the liner elements which define the first and second interstitial spaces;

(e) welding adjacent edges of the liner elements positioned as in step (c), welding the edges of the liner elements onto the supporting surfaces and welding said at least one strap to the liner elements, thereby forming an internal surface of the lining which is totally sealed with a non-corroded area of the lining; and (f) leaving an interrupted stretch of weld beneath the strap positioned as in step (d), so as to allow communication between the first and second interstitial spaces, said step of leaving interrupted stretches further comprises leaving an average number of from 1.5 to 2.5 interrupted stretches having a length of between 5 and 30 mm for each liner element.

2. Method according to claim 1, wherein said equipment is part of a plant for the production of urea.

3. Method according to claim 2, wherein said equipment is a reactor for the synthesis of urea, or a carbamate condenser, or a carbamate decomposer.

4. Method according to claim 1, wherein the operating pressure of said equipment is between 10.13 MPa (100) and 25.33 MPa (250 atm).

5. Method according to claim 1, wherein said equipment has a volume of between 2,000 and 400,000 liters and an internal surface area in contact with the process fluids (excluding pipes) of between 8 and 450 m$^2$.

6. Method according to claim 2, wherein said anticorrosive metallic lining has a thickness of between 2 and 30 mm and is made of at least one of titanium, zirconium, lead, AISI 316L (urea grade) steel, INOX 25/22/2 Cr/Ni/Mo steel or special austenite-ferrite steels.

7. Method according to claim 1 wherein, in step (c), said liner elements are rectangular and have a thickness of between 2 and 30 mm.

8. Method according to claim 1, wherein, in step (c), said liner elements are made of at least one of titanium, zirconium titanium-zirconium alloy, INOX 25/22/2 Cr/Ni/Mo steel and special austentite-ferrite steel.

9. Method according to claim 1 wherein, in step (d), said at least one strap are square or rectangular, having dimensions of between 20 and 200 mm and a thickness of between 4 and 25 mm.

10. Method according to claim 9, wherein said at least one strap is made of the same metal or metallic alloy as the liner elements.

11. Method according to claim 1 wherein, at the end of the repair, the same weep-holes originally present in said equipment are maintained.

12. Method according to claim 1 comprising, in step (c) the formation of new metallic lining consisting of a metal which cannot be welded to the original anticorrosive lining of said equipment, wherein, in step (b), metallic straps not welded to the surface of said area subjected to corrosion are positioned, said straps being weldable to the metallic elements forming said new lining, and their positioning corresponding to the supporting lines thereof.

13. Method according to claim 12, wherein, in step (e), the sealed off welding of the new lining onto the edge of the area subjected to corrosion is carried out using a bimetallic strap whose upper part is welded to a liner element and lower part to the original anticorrosive lining of the equipment.

14. Method according to claim 2, wherein the operating pressure of said equipment is between 10.3 MPa and 25.33 MPa.

15. Method according to claim 2, wherein said equipment has a volume of between 2,000 and 400,000 liters and an internal surface area in contact with the process fluids (excluding pipes) of between 8 and 450 m$^2$.

16. Method according to claim 2 wherein, in step (c), said liner elements are rectangular and have a thickness of between 2 and 30 mm.

* * * * *